United States Patent
Freed

[19]

[11] Patent Number: 6,029,668
[45] Date of Patent: *Feb. 29, 2000

[54] ENDOTRACHEAL TUBE HOLDER HAVING BOTH A SAFETY CLAMP AND A SECURING CLAMP

[76] Inventor: M. Simon Freed, 55 Davidson's Mill Rd., North Brunswick, N.J. 08902-4751

[*] Notice: This patent is subject to a terminal disclaimer.

[21] Appl. No.: 08/919,622

[22] Filed: Aug. 28, 1997

Related U.S. Application Data

[63] Continuation-in-part of application No. PCT/US95/02564, Mar. 1, 1995, abandoned, which is a continuation-in-part of application No. 08/121,154, Sep. 13, 1993, Pat. No. 5,398,679.

[51] Int. Cl.[7] .................................................. A61M 16/00
[52] U.S. Cl. ................. 128/207.17; 128/200.26; 128/207.14
[58] Field of Search .......................... 128/200.26, 207.14, 128/207.17, 912, DIG. 26

[56] References Cited

U.S. PATENT DOCUMENTS

| | | | |
|---|---|---|---|
| 3,602,227 | 8/1971 | Andrew | 128/207.17 |
| 3,993,081 | 11/1976 | Cussell | 128/351 |
| 4,209,015 | 6/1980 | Wicks | 128/214.4 |
| 4,235,229 | 11/1980 | Ranford et al. | 128/207.17 |
| 4,249,529 | 2/1981 | Nestor et al. | 128/207.17 |
| 4,270,529 | 6/1981 | Muto | 128/200.26 |
| 4,326,515 | 4/1982 | Shaffer et al. | 128/207.17 |
| 4,329,984 | 5/1982 | Kervin | 128/207.14 |
| 4,351,331 | 9/1982 | Gereg | 128/207.17 |
| 4,449,527 | 5/1984 | Hinton | 128/207.17 |
| 4,530,354 | 7/1985 | Froilan | 128/207.17 |
| 4,548,200 | 10/1985 | Wapner | 128/207.17 |
| 4,683,882 | 8/1987 | Laird | 128/207 |
| 4,699,616 | 10/1987 | Nowak et al. | 604/180 |
| 4,774,944 | 10/1988 | Mischinski | 128/207.17 |
| 4,832,019 | 5/1989 | Weinstein et al. | 128/207.17 |
| 4,896,667 | 1/1990 | Magnuson et al. | 128/207.14 |
| 5,026,352 | 6/1991 | Anderson | 604/178 |
| 5,069,206 | 12/1991 | Crosbie | 128/207.17 |
| 5,233,979 | 8/1993 | Strickland | 128/207.14 |
| 5,251,616 | 10/1993 | Desch | 128/207.17 |
| 5,320,097 | 6/1994 | Clemens et al. | 128/207.17 |
| 5,398,679 | 3/1995 | Freed | 128/207.17 |
| 5,555,881 | 9/1996 | Rogers et al. | 128/207.17 |
| 5,558,090 | 9/1996 | James | 128/207.18 |
| 5,653,232 | 8/1997 | Rogers et al. | 128/207.17 |

FOREIGN PATENT DOCUMENTS

WO96/26756  9/1996  WIPO .

*Primary Examiner*—Aaron J. Lewis
*Attorney, Agent, or Firm*—Pierce Atwood; Chris A. Caseiro; Celia H. Leber

[57] ABSTRACT

A holder for retaining an endotracheal tube in a patient's mouth includes a pair of opposed members constructed to define a lumen when positioned adjacent each other, and a latching device constructed to allow the relative position of the opposed members to be adjusted between a first position in which said lumen is sufficiently small to securely hold the endotracheal tube, and a second position in which the lumen is sufficiently large to allow the endotracheal tube to move axially yet sufficiently small to resist radial displacement of the endotracheal tube. In use, the endotracheal tube is inserted through a patient's mouth into the tracheal lumen, the latching device is moved to its second position, the tube holder is slid over the endotracheal tube and its position adjusted axially along the length of the tube, and the latching device is moved to its first position to secure the tube holder firmly in a desired position on the endotracheal tube.

28 Claims, 11 Drawing Sheets

ENDOTRACHEAL TUBE HOLDER HAVING BOTH A SAFETY CLAMP AND A SECURING CLAMP

RELATED APPLICATIONS

This application is a continuation-in-part of International Patent Application Ser. No. PCT/US95/02564, with an International Filing Date of Mar. 1, 1995, now abandoned, which was a continuation-in-part of U.S. patent application Ser. No. 08/121,154, filed Sep. 13, 1993, which issued as U.S. Pat. No. 5,398,679 on Mar. 21, 1995.

BACKGROUND OF THE INVENTION

The invention relates to holders for endotracheal tubes.

An endotracheal tube is generally inserted in the tracheal lumen of a patient, through the patient's mouth, to deliver air to the patient's lungs when the mouth, throat or trachea of the patient is obstructed.

It is important that the endotracheal tube be securely retained in the patient's mouth to prevent accidental removal of the tube from the tracheal lumen, which could result in asphyxiation. It is also important to minimize damage to the mucous membranes of the larynx and trachea caused by rubbing of the tube against the membrane. The tube must be retained in a manner that will secure it against shifts in the patient's position, movement of attached ventilating equipment and slippage. Moreover, the patient should be prevented from biting down on the tube and either cutting it or closing off the air supply through the tube.

Until relatively recently, endotracheal tubes were typically held in place by tape. Retaining the tube in this manner was difficult to accomplish and unreliable, as the tape would not always adhere to the patient's skin and required a relatively high degree of skill to apply quickly and securely. This method also made it impractical to adjust the orientation of the tube in the tracheal lumen after the initial insertion, and removal of the tape from the patient's skin and facial hair was often traumatic.

To remedy this situation, various types of endotracheal tube holders have been developed. These holders are thought to allow the tube to be more quickly and easily inserted and positioned, and may include means for preventing the patient from biting the tube. However, typically these holders do not allow the patient's mouth to be easily accessed by medical staff, e.g., for the administration of medicaments or cleansing and swabbing. Also, many such devices require two-handed operation and are not readily adjustable.

SUMMARY OF THE INVENTION

The present invention features an improved endotracheal tube holder which allows a patient's mouth to be readily accessed when the endotracheal tube and holder are in place, and which is easily operated and adjusted with one hand. The tube holder provides good resistance to biting, and is comfortable to the patient. The tube holder also can be positioned prior to positioning the tube, and the axial position of the holder relative to the tube can be readily adjusted to a desired position even during use of the tube.

The endotracheal tube holder includes (a) a pair of opposed members constructed to define a lumen when positioned adjacent each other, and (b) a latching device constructed to allow the relative position of the opposed members to be adjusted between a first position, in which the lumen is sufficiently small to securely hold the endotracheal tube, and a second position, in which the lumen is sufficiently large to allow the endotracheal tube to move axially yet sufficiently small to resist radial displacement of the endotracheal tube. The term "lumen" as used herein, refers to any structure that can be positioned around the outer surface of an endotracheal tube. For example, the lumen need not define a continuous cylinder but could instead be a discontinuous structure having separate arcuate portions that together provide sufficient support to the outer surface of the endotracheal tube to retain the tube.

The invention also features a method of inserting and retaining an endotracheal tube in the tracheal lumen of a patient. The method includes (a) inserting the endotracheal tube through the patient's mouth into the tracheal lumen; (b) providing an endotracheal tube holder as described above; (c) introducing the endotracheal tube into the lumen defined by the endotracheal tube holder; (d) placing the latching device in its second position; (e) adjusting the position of the endotracheal tube holder axially along the length of the endotracheal tube until the endotracheal tube holder is in a desired position; and (f) placing the latching device in its first position, thereby securing the endotracheal tube holder firmly in position on the endotracheal tube. Preferably, the endotracheal tube holder is secured to the patient's head prior to step (e) above.

In one aspect of the invention, the endotracheal tube holder includes a first member, a second member, positioned in opposed, spaced relation relative to the first member, a hinge constructed to allow the first member to pivot with respect to the second member, and a latching device constructed to allow the relative position of the opposed members to be adjusted. The first member includes a first pair of wing members and a first portion disposed between the first pair of wing members, and the second member includes a second pair of wing members and a second portion disposed between the second pair of wing members. The first and second pairs of wing members are dimensioned and arranged so that when the endotracheal tube holder is in a closed position a region of each wing of the first member is adjacent to a region of a corresponding opposed wing of the second member. The first and second portions are arranged and dimensioned so that when the first and second members are so positioned the first and second portions define a lumen dimensioned to receive the endotracheal tube. The latching device includes a safety clamp and a securing clamp. The safety clamp is disposed in a region of the opposed wings and includes a portion which provides interference engagement between the wings to limit the extent to which the first member and second member can pivot about the hinge to a predetermined maximum angle. This angle is sufficiently large to allow the position of the endotracheal tube in the housing to be adjusted axially, and sufficiently small so that the tube cannot be radially displaced from the endotracheal tube holder when the safety clamp is engaged. The securing clamp is disposed in a region of the opposed wings and is constructed to be movable between a first position and a second position. In the first position, the first and second members are allowed to pivot to the extent allowed by the safety clamp, to allow for axial adjustment of the endotracheal tube within the lumen. In the second position, the first portion and the second portion are sufficiently close to each other to engage the tube and limit axial movement of the tube relative to the endotracheal tube holder.

In a preferred aspect of the invention, the endotracheal tube holder further includes a deflection spring on which one of the first and second portions is mounted. The deflection spring comprises a pair of cantilevered members. Each cantilevered member is positioned between an end of the portion and the corresponding wing that extends from the portion at that end. The elongate members are biased toward the longitudinal axis of the lumen, and constructed to deflect away from the longitudinal axis of the lumen in response to pressure, e.g., when the portion is pressed against the endotracheal tube. This feature allows the endotracheal tube holder to accommodate endotracheal tubes having a range of outer diameters. Preferably, the deflection spring is formed of a rigid or semi-rigid polymeric material having a Young's Modulus of from about $1 \times 10^{-5}$ to $1 \times 10^{-6}$ psi, e.g., medical grade vinyl. It is also preferred that the deflection spring comprise a pair of curved elongate members disposed on either side of the arcuate portion that will define the lumen. More preferably, the curve of the elongate members has a radius of curvature of from about 0.5 to 2.0 inches. In this embodiment, the other portion that defines the lumen is preferably U-shaped.

Preferred endotracheal tube holders may include any of the following features. Each of the first and second portions comprises a semi-cylindrical member. The endotracheal tube holder further comprises a bite block extending axially from the lumen. The bite block has a rectangular cross-section. A soft material, preferably having a durometer rating of 80 or less covers the bite block. The bite block includes a foam or elastomeric sheath. The first member is joined to the second member by a flexible hinge extending between a first wing of the first member and an opposed first wing of the second member. The wings are arranged and dimensioned so that a major portion of each wing is removed from a horizontal plane defined by the longitudinal axis of the lumen defined by the portions and a substantially horizontal line taken radially across the lumen. A first portion of each wing, adjacent the semi-cylindrical portion, extends out of the horizontal plane, and a second more remote portion of each wing extends away from the lumen in a plane substantially parallel to the horizontal plane. The lumen defined by the first and second portions includes a plurality of raised structures on its inner surface. In one embodiment, the safety clamp and securing clamp each comprise a resilient member extending from one portion through an aperture in the other portion. The resilient member includes (a) a first latch member adapted to engage provide interference engagement between the portions, and (b) a first release member constructed to disengage the first latch member. In the safety clamp, the resilient member is dimensioned to allow the first and second portions to pivot about the hinge to define a maximum angle of less than about 30 degrees, preferably from about 5 degrees to 10 degrees. In the securing clamp, the resilient member is dimensioned so that when the latch member is engaged the lumen that is defined by the first and second portions has a predetermined diameter that is substantially equal to that of the outer diameter of the endotracheal tube. In alternative embodiments, the safety and securing clamps may comprise a plurality of detents positioned on a first member and a detent-engaging structure on an opposed member, the detents being positioned so that selective engagement of a detent by the detent-engaging structure will provide the safety clamp and securing clamp functions described above.

Other features and advantages of the invention will be apparent from the following description of presently preferred embodiments, and from the claims.

BRIEF DESCRIPTION OF THE DRAWINGS

FIGS. 6 and 6a are cross-sectional side views, taken along line 6—6 in FIG. 5, of, respectively, the upper and lower members of the endotracheal tube holder of FIGS. 5—5a.

FIG. 9 is a top view of the bite block sheath used in the endotracheal tube holder shown in FIGS. 5—5a. FIGS. 9a–c are cross-sectional views of the bite block sheath, taken along lines A—A, B—B and C—C in FIG. 9.

DESCRIPTION OF THE PREFERRED EMBODIMENTS

Figure 1:
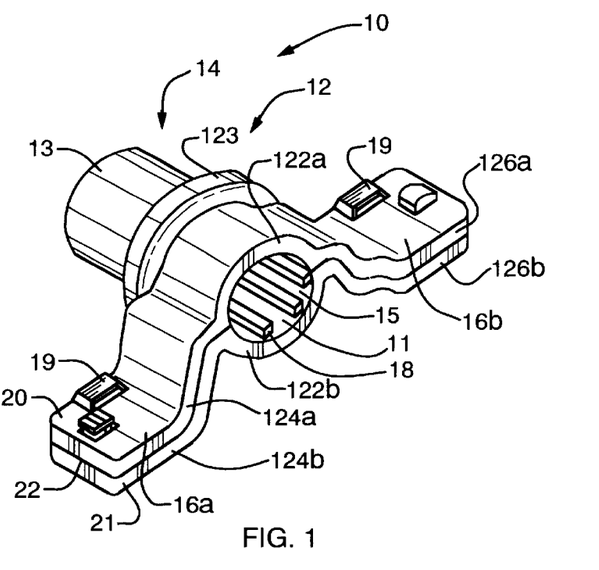
FIG. 1 is a perspective view of an endotracheal tube holder according to one embodiment of the invention.
Figure 2:
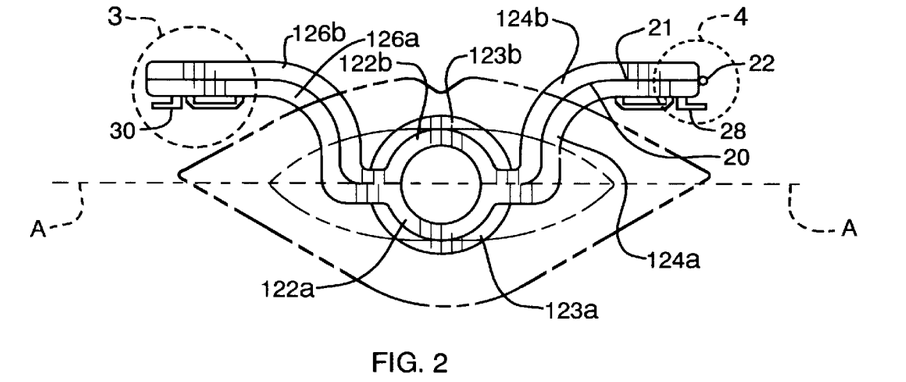
FIG. 2 is a front view of the endotracheal tube holder of FIG. 1.

Referring to FIGS. 1 and 2, endotracheal tube holder 10 includes an integral housing 12 having a "clamshell" type structure, i.e., housing 12 comprises two halves, upper half 20 and lower half 21, which are joined by a flexible hinge 22. Each half comprises a semi-cylindrical portion 122a, 122b positioned between a pair of wings 124a, 124b, and 126a, 126b.

When hinge 22 is in a closed position, as shown in FIG. 1, semi-cylindrical portions 122a, 122b form an annular sleeve 14. Sleeve 14 defines a lumen 15, dimensioned to receive an endotracheal tube (not shown), and includes a bite block 13 constructed to be positioned in a patient's mouth. Sleeve 14 is preferably formed of a rigid, resilient material, e.g., polypropylene, which has sufficient rigidity to act as a bite guard for the endotracheal tube, preventing the patient from damaging or closing the tube by biting down on it, and sufficient resiliency to provide cushioning for patient comfort. Preferably, sleeve 14 has a plurality of longitudinal ribs 18 on its inner surface 11, to provide a more positive grip of the sleeve about the endotracheal tube extending therethrough. If desired, the ribs 18 can have a different configuration, e.g., can be arranged spirally or circumferentially about the inner surface 11. A flange 123, having portions 123a, 123b, extends radially from the outer surface of the sleeve in a manner to aid in longitudinal positioning of the sleeve by engaging gently against a patient's upper and lower front teeth, as described in more detail below.

Each pair of adjacent wings, i.e., pairs 124a, 124b and pairs 126a, 126b, forms a wing structure 16a, 16b when hinge 22 is in a closed position, as shown in FIGS. 1 and 2. The two wing structures curve upwardly, out of a plane defined by the axis of the tube and sleeve 14 and a horizontal line A across the patient's mouth. This upward curve allows easy access to the patient's mouth on either side of the housing in a manner to facilitate more thorough and efficient mouth care. Two neck/head strap holders 19 are mounted on the housing, one on each wing, to receive a strap (not shown) which is fastened behind the patient's neck or head.

The diameter of lumen 15 defined by sleeve 14 is determined by the spacing between the semi-cylindrical members. To adjust this spacing, and to hold the upper and lower halves relatively close together, so that the holder can be manipulated with one hand, the housing is provided with a pair of clamps. In the preferred embodiment shown, the housing includes a securing clamp 30 on wing 16b and a safety clamp 28 on wing 16a.

Safety clamp 28, which is closest to hinge 22, is provided to act as a stop, limiting the amount of separation between the two halves. Preferably, when the hinge is open to the fullest extent allowed by the safety clamp, a lumen is still defined by the semi-cylindrical portions at least to an extent to prevent radial displacement of the tube from the lumen. Thus, the safety clamp allows the diameter of the lumen to be increased sufficiently to allow axial adjustment of the endotracheal tube, without allowing the two halves to become so separated that it is difficult to close them with one hand.

Figure 4:
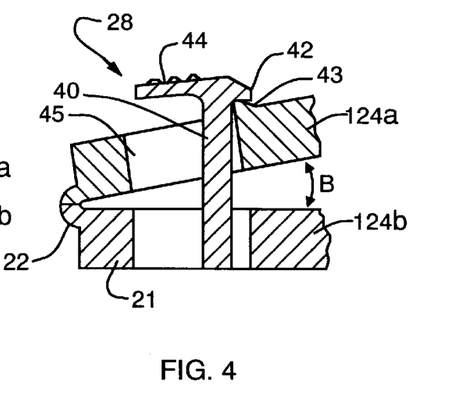
FIG. 4 is an enlarged cross-sectional view of Detail 4 in FIG. 2.

Referring to FIG. 4, safety clamp 28, shown in detail, includes a resilient member 40 which extends upwardly from wing 124b of the lower half 21 of the housing, through aperture 45 in opposed wing 124a. Resilient member 40 includes a latch member 42 and a release member 44. Wing 124a defines a shoulder 43, positioned for engagement by latch member 42. Resilient member 40 is dimensioned so that, when latch member 42 and shoulder 43 are engaged, as shown in FIG. 4, the two halves of the housing can be separated (pivoted about hinge 22) to define a maximum angle B there between. Preferably, angle B is less than about 30 degree(s), more preferably angle B is about 5 degree(s) to 10 degree(s). If it is desired to open the two halves beyond the extent allowed by the safety latch, latch member 42 may be released from shoulder 43 by depressing release member 44.

Securing clamp 30, when engaged, clamps the housing around the tube, thereby securely holding the tube against both axial and radial displacement, and, when disengaged, allows the housing to open to the extent allowed by safety clamp 28.

Figure 3:
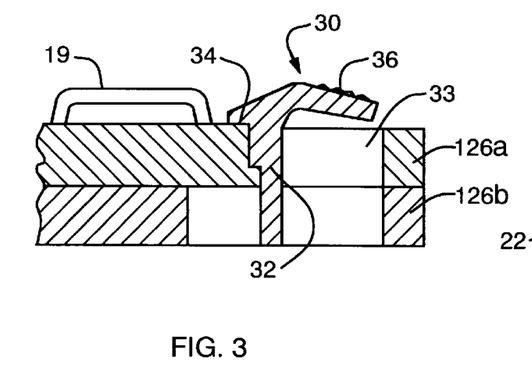
FIG. 3 is an enlarged cross-sectional view of Detail 3 in FIG. 2.
Figure 3A:
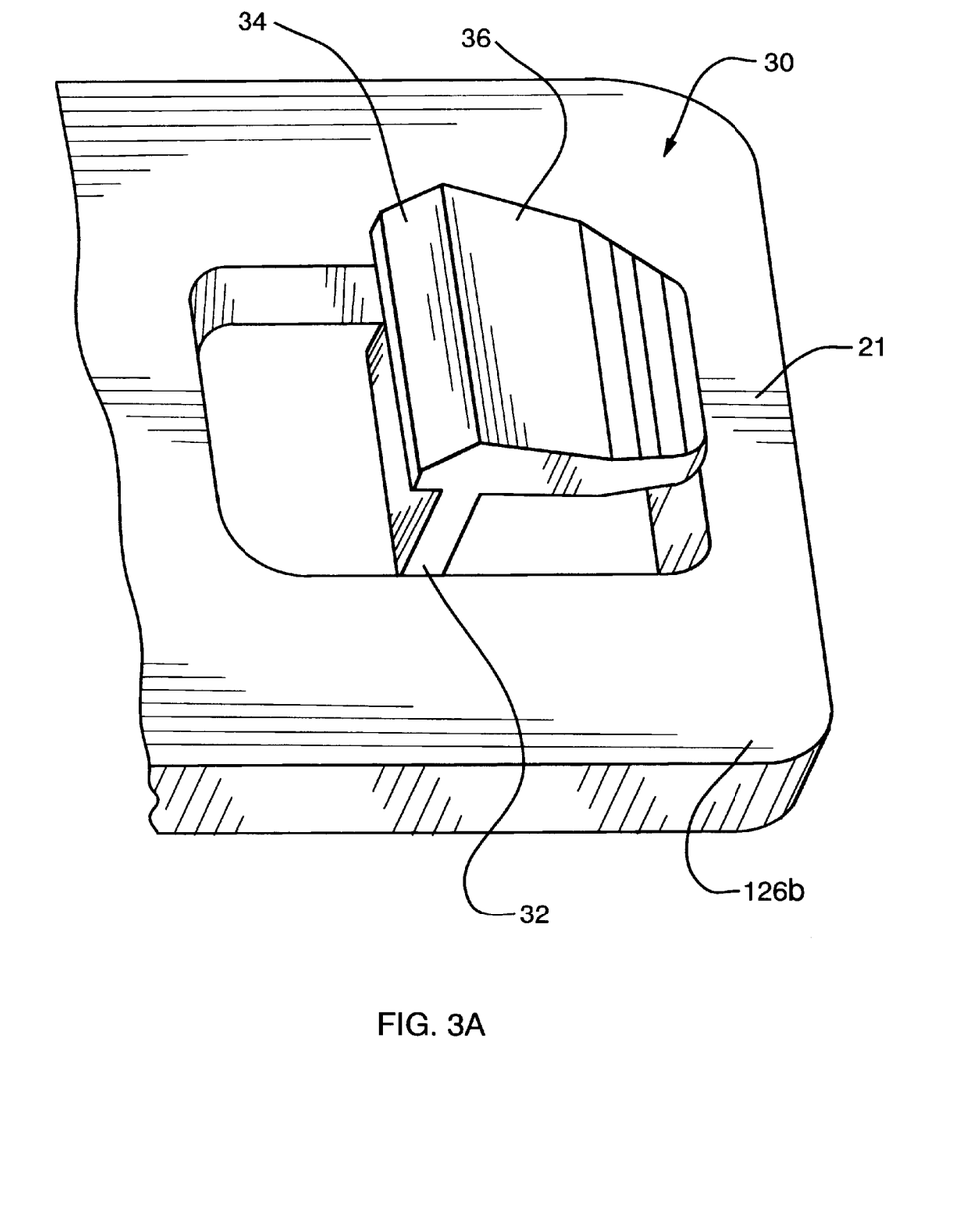
FIG. 3a is a highly enlarged perspective view of the clamp shown in FIG. 3.

Referring to FIGS. 3 and 3a, securing clamp 30, shown in detail, comprises resilient member 32, which extends upwardly from wing 126b of lower half 21, through aperture 33 in wing 126a. Resilient member 32 includes latch member 34 and release member 36. Securing clamp 30 functions in the same manner as does safety clamp 28, i.e., the latch member engages the upper wing until it is released therefrom by depressing the release member. (Apertures in the wings 124b, 126b (FIGS. 3a and 4, respectively) facilitate the manufacturing process.)

In use, an endotracheal tube is first inserted through the patient's mouth into the tracheal lumen. Then, with the safety clamp closed and the securing clamp open, the sleeve of the holder is slid over the endotracheal tube. The position of the holder can then be adjusted axially along the tube until the holder is in a desired position, preferably with the flange portions engaged gently against the patient's teeth. A neck/head strap, attached to the wings on either side of the housing, is then typically fastened about the neck or head of the patient. When a desired position is achieved, the securing clamp is then closed, typically with one hand, securing the tube firmly in position within the holder. If further adjustment of the holder later becomes necessary, this can easily be accomplished by unfastening the securing clamp, sliding the tube axially within the lumen of the holder, and refastening the securing clamp.

Figure 5:
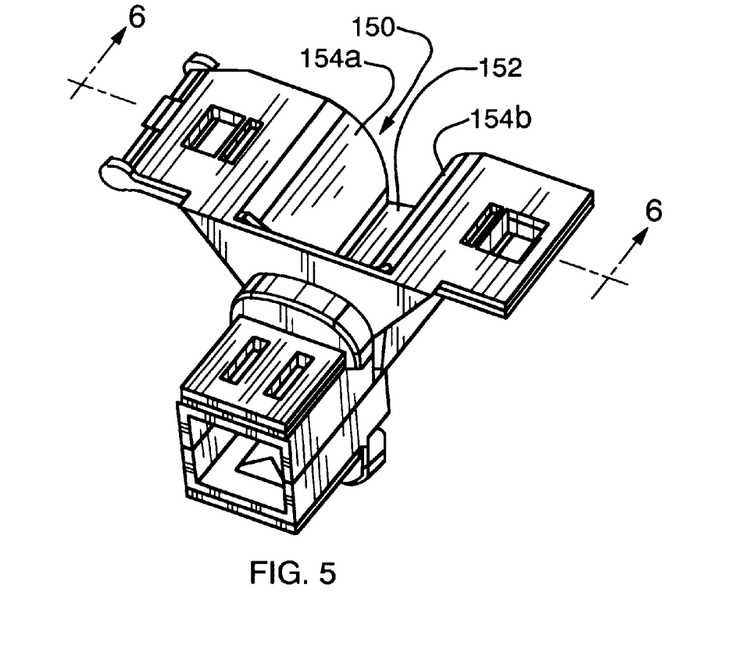
FIGS. 5 and 5a are perspective and end views, respectively, of an endotracheal tube holder according to an alternate embodiment of the invention.
Figure 5A:
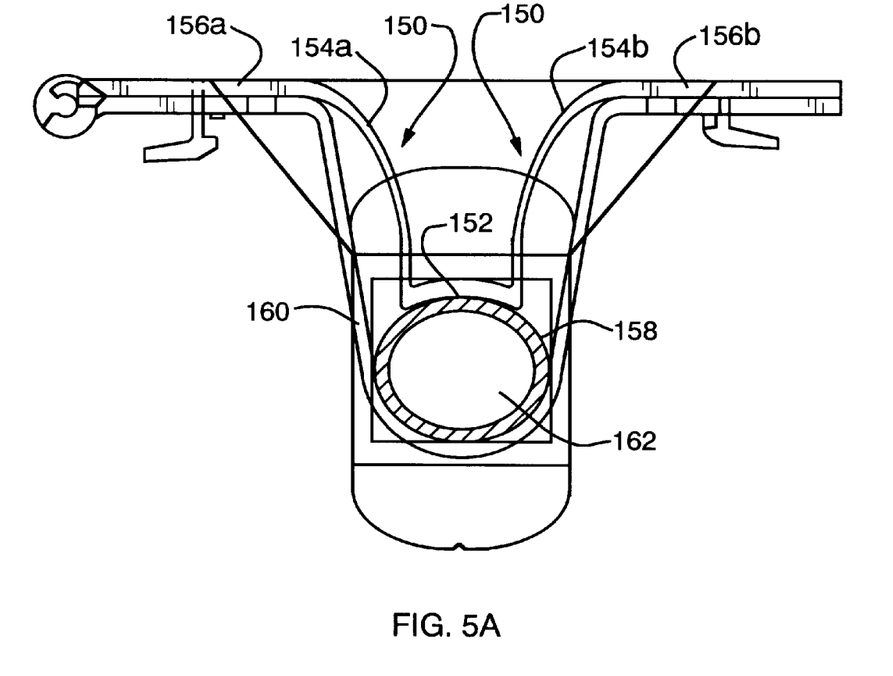
Figure 6:
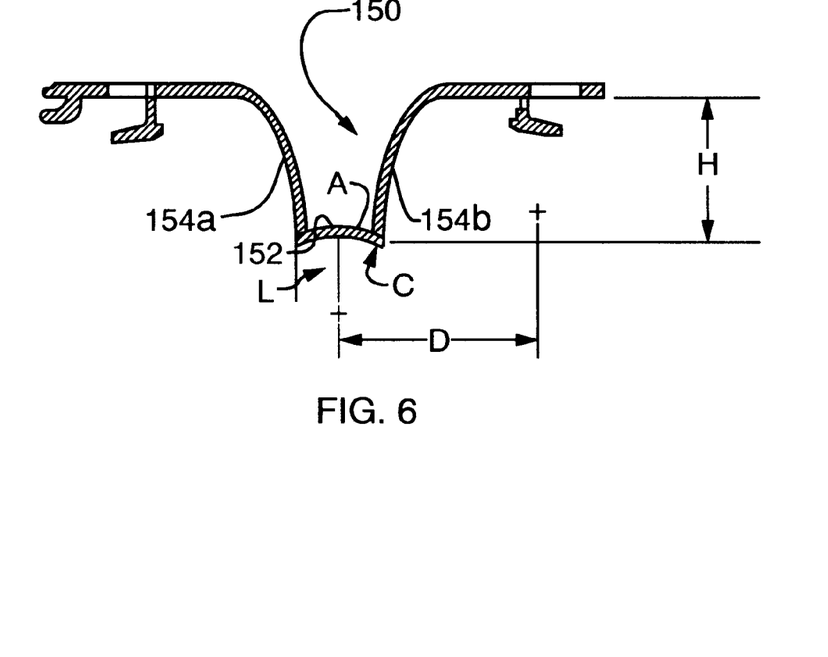
Figure 6A:
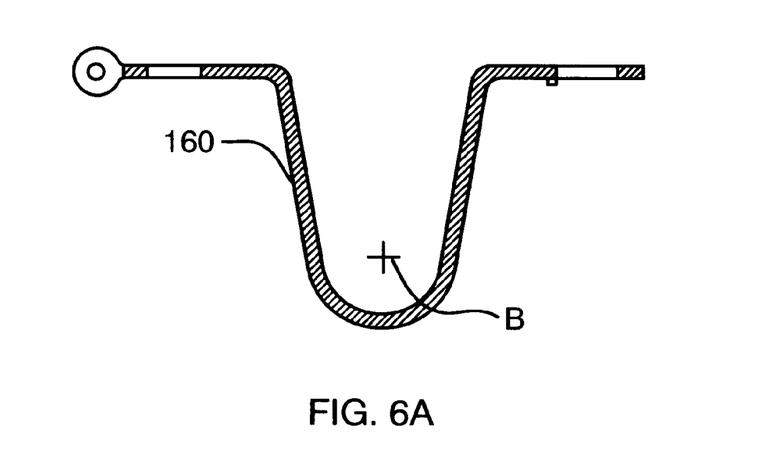
Figure 7:
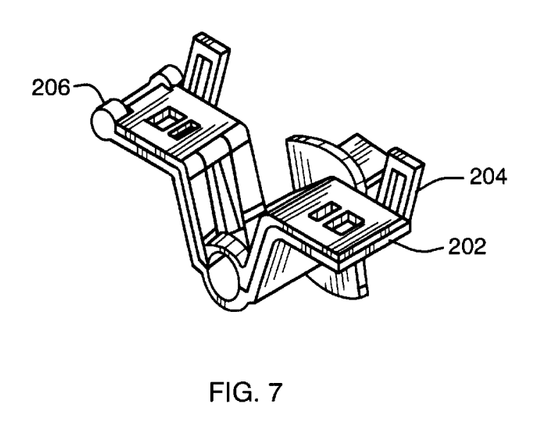
FIGS. 7—7f and 8—8f are views, taken from different angles, of endotracheal tube holders according to two further alternate embodiments of the invention.
Figure 7A:
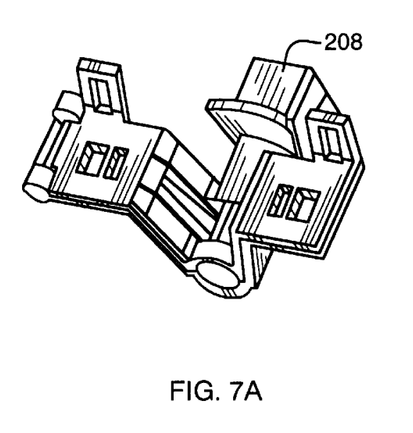
Figure 7B:
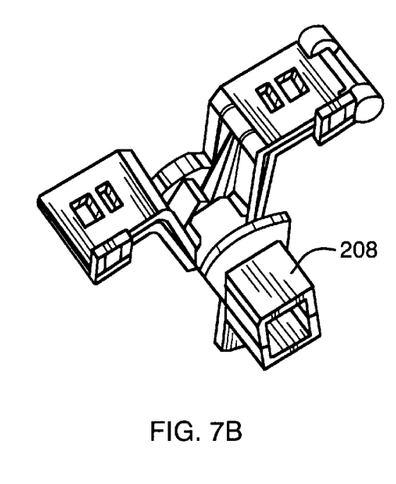
Figure 7C:
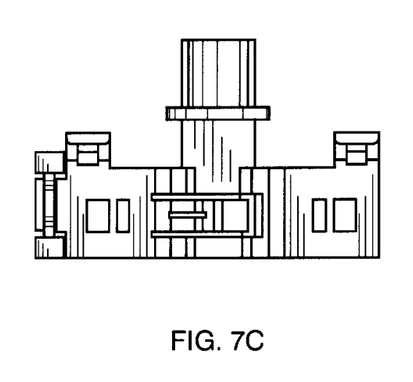
Figure 7D:
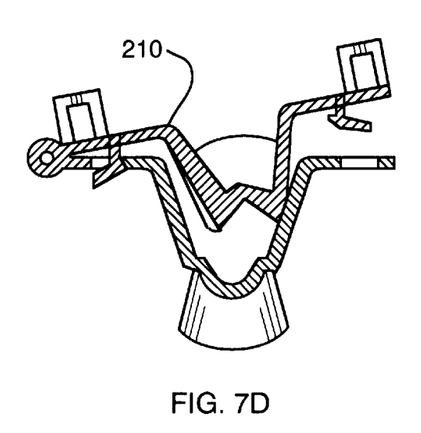
Figure 7E:
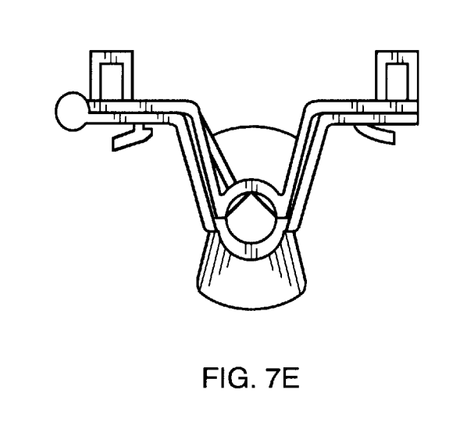
Figure 7F:
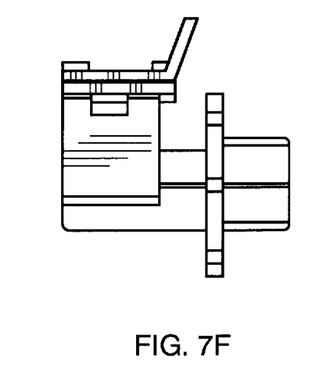

In an alternate embodiment, shown in FIGS. 5 and 5a, the endotracheal tube holder further includes a deflection spring 150 on which upper arcuate portion 152 is mounted. The deflection spring comprises a pair of curved, elongate cantilevered members 154a, 154b. One cantilevered member is positioned between each end of the arcuate portion 152 and the corresponding wing 156a, 156b that extends from the portion at that end. The cantilevered members are biased toward the longitudinal axis of the lumen, and constructed to deflect away from the longitudinal axis of the lumen in response to pressure, e.g., when the arcuate portion 152 is pressed against the endotracheal tube 158. This biasing and deflection allows the endotracheal tube holder to accommodate endotracheal tubes having a range of outer diameters. The lower portion 160, that with arcuate portion 152 defines lumen 162, is preferably U-shaped, as shown in FIG. 6a, to define a seat for the endotracheal tube. It is preferred that the lower portion 160 have a radius of curvature of from about 0.15 to 0.35 inches, and be sufficiently strong to resist deflection when the endotracheal tube holder is closed.

Preferably, the deflection spring has the following properties: (a) it is capable of repeated deflection, during closure of the holder, without failure, (b) it exhibits the desired degree of deflection in response to the pressures which are exerted during closure of the endotracheal tube holder, (c) it is resistant to compression set, and (d) it is formed of a material that is inert with respect to the material of the endotracheal tube and which is safe to use near or in a patient's mouth.

Suitable materials for the deflection spring include rigid or semi-rigid polymeric materials that have a Young's Modulus of from about $1 \times 10^{-5}$ to $1 \times 10^{-6}$ psi. One suitable material is a medical grade vinyl having the above modulus, e.g., 87402 GEON vinyl, commercially available from The GEON Co., 6100 Oak Tree Blvd., Cleveland, Ohio 44131. The thickness, overall height, and radius of curvature of the elongated members 154a, 154b (see dimensions T, H and R, respectively) and the distance from the center of arcuate portion 152 to the safety or securing clamp (dimension D) will also effect the durability, compression set and deflection of the deflection spring. For 87402 GEON vinyl, the elongated members are preferably from 0.040 to 0.100 inches thick and from 0.5 to 2.5 inches long, each of the cantilevered elongate members has a radius of curvature of from about 0.5 to 2.0 inches, and the distance D is from about 0.70 to 1.1 inches. It is also important that the length and curvature (L and C) of the arcuate portion 152 be selected so that the arcuate portion does not deflect significantly during closure of the device. For 87402 GEON vinyl, it is preferred that the arcuate portion 152 have a length of 0.3 to 0.5 inches and a radius of curvature of 0.4 to 0.5 inches. For other plastics, the preferred dimensions will be different. Also, if one of the above dimensions is varied, the other dimensions generally also must be varied. Preferred dimensions for a given material and given use requirements can be readily determined by using finite element analysis or by using the equations shown in the Equations section, below, as an algorithm in a MATHCAD software program or similar computational software program. If desired, the thickness of each cantilevered member can be tapered along the length of the member, to provide a non-linear spring. The preferred degree of taper depends upon the material used and the requirements for the spring, and could be readily determined for a particular material and given use conditions.

Equations

The following equations can be used to determine the loads and stresses on a deflection spring and the deflection of the spring based on the properties of the polymeric material used, the cross-sectional area of the elongated members, and the diameter of the endotracheal tube. These equations will allow the artisan to predict the behavior of a deflection spring having a given design, and thus determine the dimensions and material required for a given application. The numerical values given below by way of example were those used for 87402 GEON vinyl and forces measured using the given endotracheal tube dimensions.

First, the following method was used to determine the time constant (T) for a given polymeric (visco-elastic) material:

Time Constant Calculations $\sigma$ = applied stress  t = time  $\epsilon$ = strain  E = modulus
$E = \sigma_i/\epsilon_i$
$\sigma = 1 \times 10^3$ psi
$\epsilon = 0.002$ (stress and strain were measured when the endotracheal tube holder was initially closed)

$i = 0 \ldots 3$ $t = 0$
$10^5$ sec (3 hours)
$10^6$ sec (11 days)
$10^7$ sec (115 days)

$E = 4 \times 10^5$ psi
$3.1 \times 10^5$ psi
$2.8 \times 10^5$ psi
$2.4 \times 10^5$ psi $\eta$ = solid state viscosity $\eta_i = \dfrac{\sigma(t_i)}{\varepsilon}$ $\eta = 0$
$5 \times 10^{10}$ psi-sec
$5 \times 10^{11}$ psi-sec
$5 \times 10^{12}$ psi-sec Because the matrix values above were so close to each other, the modulus (E) was assumed to be constant in the following equation.

$\tau_i = \dfrac{\eta_i}{E_i}$ $\tau = 0$
$1.613 \times 10^5$ sec
$1.786 \times 10^6$ sec
$2.083 \times 10^7$ sec Next, using the above time constant values, the stress relaxation modulus was calculated as follows:

Stress Relaxation Modulus Calculation $Et_i = E_i e^{(ti/\tau_i)}$ $Et_i = 4 \times 10^5$ psi
$1.668 \times 10^5$ psi
$1.599 \times 10^5$ psi
$1.485 \times 10^5$ psi Thus, using the GEON vinyl, the stress relaxation modulus decreased to half its initial value in 3 hours.

The following are calculations for a beam in compression with pivots at both ends. These equations utilize the plastic behavior of the polymer which has been previously determined.

Off to the right is a figure of a beam in compression with rollers affixed to a surface. This simulates the compressive action which occurs with the possibility of bending occurring in the middle of the beam once it's gone past the yield point. This beam is completely free to rotate at either end.

Electric Loading
Stress Calculations were:
  P=load
  A=cross sectional area
  M=moment
  I=moment of inertia
  c=distance from outer edge (centroid)
  $\sigma_c$=stress in compression for this case
  ec=eccentricity (distance off center)
  k=radius of gyration
Stress Calculations $ec := 2 \cdot \text{in}$ $P := 18 \cdot \text{lb}f$ $b := .375 \cdot \text{in} \quad w := .0875 \cdot \text{in} \quad 1 := 2 \cdot \text{in} \quad \text{Assuming that } w < b$ $A := b \cdot w \quad c := .5 \cdot w$ -continued $$I := \frac{1}{12} \cdot b \cdot w^3 \text{ (for a rectangular beam)}$$

1/c must be >120 to consider buckling.

$$\frac{1}{c} = 45.714$$

$$k = \sqrt{\left(\frac{I}{A}\right)}$$

$$\delta_1 := ec \cdot \left[\sec\left[\left(\frac{1}{2}\right) \cdot \sqrt{\frac{P}{(Et_i \cdot I)}}\right] - 1\right]$$

Maximum Moment Calculation $$M = P(ec + \delta)$$

$$\delta := \begin{bmatrix} .01 \\ .0625 \\ .125 \\ .25 \end{bmatrix} \cdot in$$

These values represent the known deflections due to the different hose diameters.

The formula below calculates the stresses in compression given the above conditions.

$$\sigma c := \frac{P}{A} + \frac{P \cdot (ec + \delta) \cdot c}{I}$$

This stress value was interpolated from the creep rupture data to represent the applied stress encountered between 3 hours and 11 days.

$$\sigma c := 6 \cdot 10^3 \cdot psi$$

The equation was manipulated to solve for the resulting loads for each diameter.

$$P_i := \frac{\sigma c}{\frac{1}{A} + \frac{(ec + \delta_i) \cdot c}{I}}$$

$$P = \begin{bmatrix} 12.784 \\ 10.362 \\ 8.455 \\ 6.18 \end{bmatrix} \cdot lbf$$

Assuming that the plastic members deflect as shown by δ matrix these are the resulting loads. This is a linear analysis at t=0. According to the modulus calculations, the applied load will decrease by half in 3 hours.

Other embodiments are within the claims.

For example, where desired for increased security against accidental or inadvertent release, e.g., due to movement or actions by a patient, a second securing clamp may be provided, preferably at a right angle to the first securing clamp, so that two hands must be used to release the device.

In the endotracheal tube holders shown in FIGS. 5—5a, 7—7f and 8—8f, the upper and lower members are separate members 202, 204, joined at a hinge 206. Hinge 206 can be any type of hinge suitable for joining plastic members, of which many are known in the art.

Figure 8:
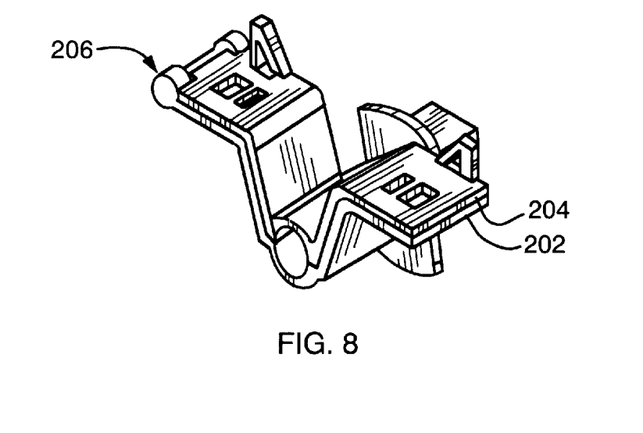
Figure 8A:
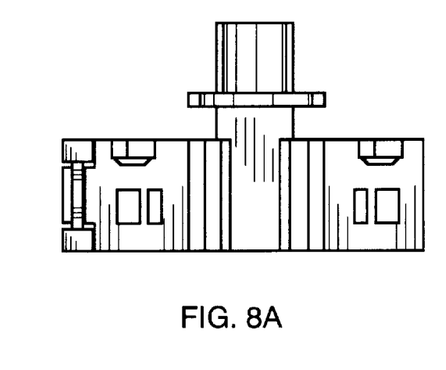
Figure 8B:
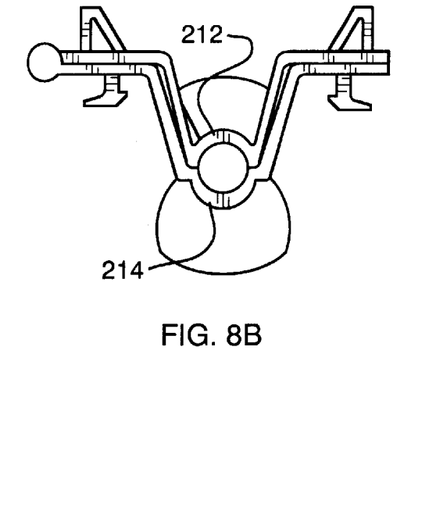
Figure 8C:
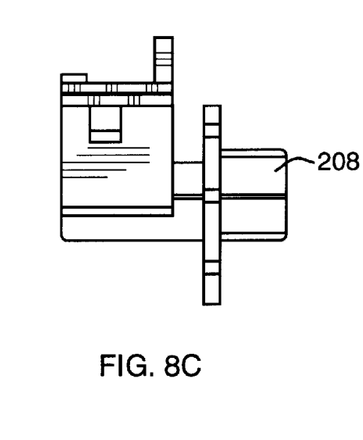
Figure 8D:
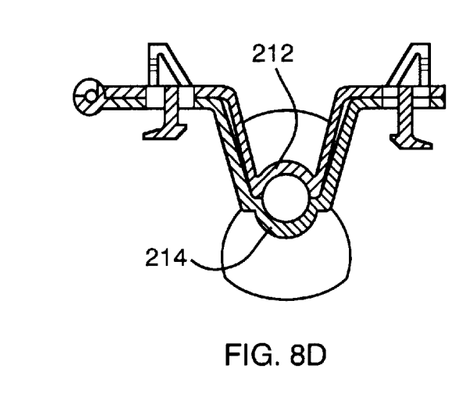
Figure 8E:
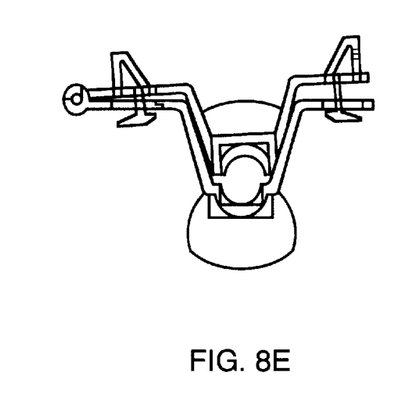
Figure 8F:
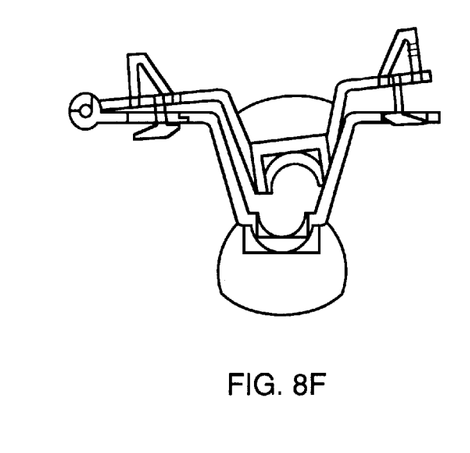
Figures 9, 9A, 9B:
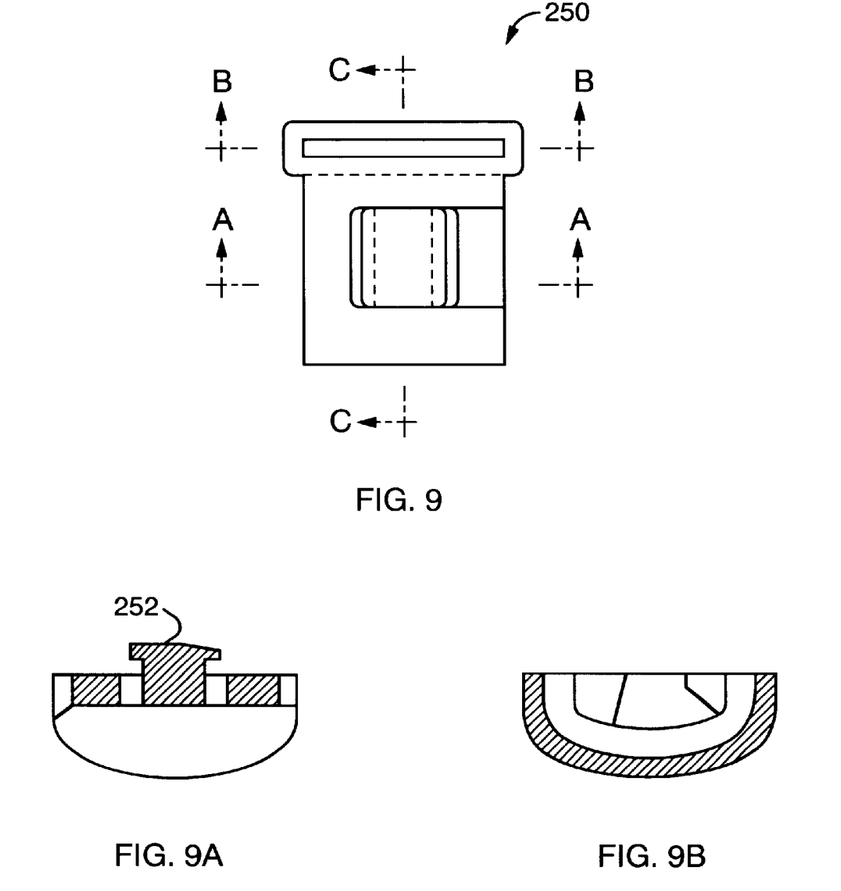
Figure 9C:
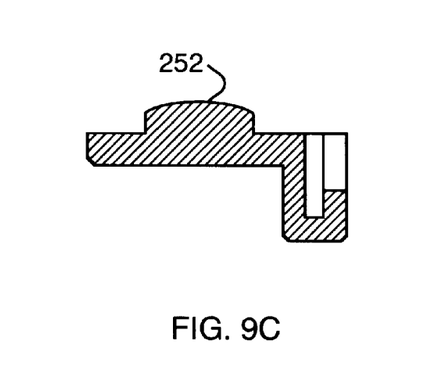

The holders shown in FIGS. 5—5a, 7—7f and 8—8f also include a bite block 208 that is square in cross-section. The bite block can, alternatively, have any other desired cross-sectional shape. As shown in FIGS. 8—8f and in detail in FIG. 9, the bite block can be covered with a flexible sheath 250 or a coating or layer of soft material, to improve patient comfort. The bite block sheath 250, shown in detail in FIGS. 9—9c, is formed of soft elastomeric material, e.g., a material having a durometer of less than 80, preferably about 60. Vinyls having a suitable softness are commercially available from The GEON Co., Cleveland, Ohio. The sheath can also be formed of foam or any other soft cushioning material that may be used in a patient's mouth. As shown in FIGS. 9a and 9c, the sheath 250 is attached to the bite block by an interference fit between the dome portion 252 of the sheath and an aperture 254 in the bite block.

As shown in FIGS. 8—8f, the first and second portions 212, 214, which together define the lumen, have a semi-elliptical cross-section, rather than a semi-cylindrical shape, to allow tubes having a range of outer diameters to have at least two points of contact with the lumen. The cross-section can also be V or U shaped. Other cross-sections that will together define a lumen can also be used. For example, in the embodiment shown in FIGS. 5 and 5a, and described above, first portion 212 has an arcuate cross-section, describing a small arc, while second portion 214 has a U-shaped cross-section.

Figure 10:
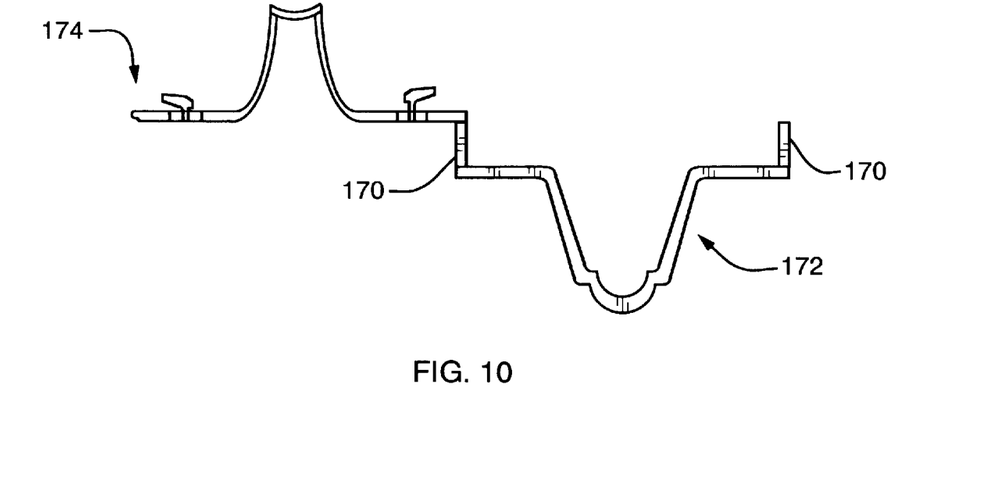
FIGS. 10—10b are schematic side views of an endotracheal tube holder according to yet another embodiment of the invention in open, semi-closed and closed positions, respectively.
Figure 10A:
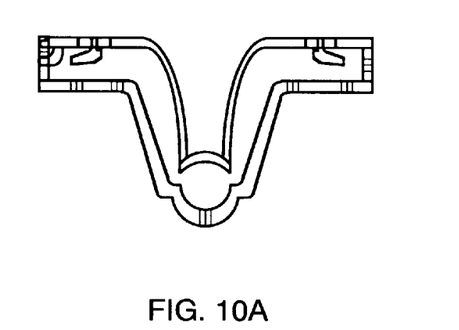
Figure 10B:
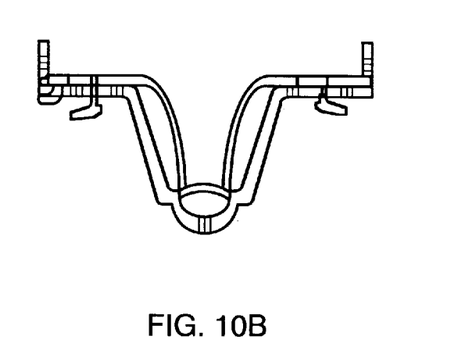

An alternate embodiment is shown in FIGS. 10—10b in which the endotracheal tube holder is latched by pushing down equally on both sides of the lumen. To accomplish this type of latching, extensions 170 are provided at each end of the lower member 172 and are constructed to slidingly engage the corresponding ends of upper member 174. In this embodiment, the safety clamp is constructed to be engaged when the upper and lower members are in the position shown in FIG. 10A, and the securing clamp is constructed to be engaged when the members are in the position shown in FIG. 10B.

Figure 11:
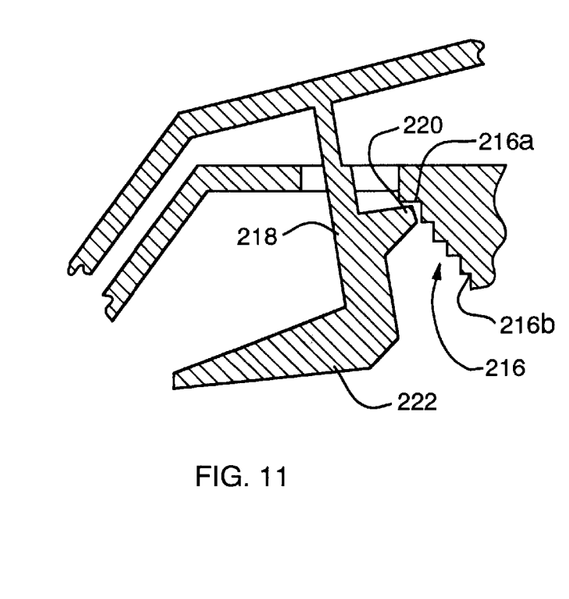
FIGS. 11 and 12 are partial enlarged cross-sectional side views of latch mechanisms according to alternate embodiments of the invention.
Figure 12:
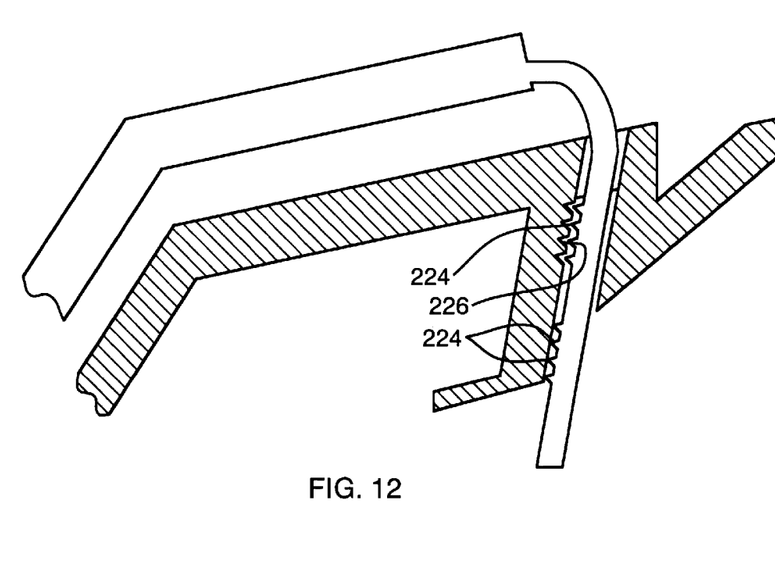

Additionally, although it is generally preferred that the safety clamp and securing clamp be on opposite sides of the lumen (this prevents inadvertent opening of the device by a patient), the safety clamp and securing clamp can be disposed on the same side of the lumen. This can be accomplished in many ways, as will be appreciated by the artisan. Two examples are shown in FIGS. 11 and 12. In FIG. 11, one of the upper and lower members includes step-like detents 216 and the other member includes a resilient member 218 having a protrusion 220 shaped to engage detents 216. Deflection of the resilient member 218, by depressing latch member 222, allows the protrusion to be moved to and engaged with a detent (e.g., 216a) in a position in which the lumen is small enough to securely hold the tube (thus acting as the securing clamp) or with another detent (e.g., 216b) in a position in which the lumen is large enough to allow the tube to move axially but small enough to retain the tube radially (thus acting as the safety clamp). This embodiment is also advantageous in that different tube outer diameters can be accommodated by providing many detents, as shown, and selecting an appropriate detent for the given tube diameter to provide each of the securing and safety clamp functions. In one of the many possible alternate embodiments, shown in FIG. 12, one of the upper and lower members includes a plurality of teeth 224, positioned in two spaced sets, and the other member includes a plurality of notches 226 on the other member dimensioned and arranged to engage one set of teeth. By moving the toothed member from a position in which one set is engaged to a position in which the other set is engaged, the size of the lumen can be varied to provide the safety clamp and securing clamp functions.

What is claimed is:

1. An endotracheal tube holder for retaining an endotracheal tube in a patient's mouth comprising:
    a pair of opposed members constructed to define a lumen when positioned adjacent each other; and
    a latching device constructed to allow the relative position of the opposed members to be adjusted between a first position in which said lumen is sufficiently small to securely hold the endotracheal tube, and a second position in which the lumen is sufficiently large to allow the endotracheal tube to move axially yet sufficiently small to resist radial displacement of the endotracheal tube.

2. The endotracheal tube holder of claim 1 wherein said pair of opposed members is hinged to allow the members to pivot with respect to each other.

3. The endotracheal tube holder of claim 2 further comprising a deflection spring on which one of said arcuate portions is mounted.

4. The endotracheal tube holder of claim 3 wherein said deflection spring is formed of a polymeric material having a Young's Modulus of from about $1 \times 10^{-5}$ to $1 \times 10^{-6}$ psi.

5. The endotracheal tube holder of claim 3 wherein said deflection spring comprises a pair of curved elongate members.

6. The endotracheal tube holder of claim 5 wherein the radius of curvature of said curved members is from about 0.5 to 2.0 inches.

7. The endotracheal tube holder of claim 5 wherein said elongate members are from 0.5 to 2.5 inches in length.

8. The endotracheal tube holder of claim 1 wherein said members include opposed arcuate portions to define said lumen.

9. The endotracheal tube holder of claim 1 further comprising a bite block extending from said lumen, constructed to be placed in the mouth of a patient.

10. The endotracheal tube holder of claim 1 wherein said bite block is covered with a soft material having a durometer hardness of less than about 80.

11. The endotracheal tube holder of claim 1 wherein said latch device comprises a securing clamp constructed to maintain the opposed members in said first position and a safety clamp constructed to maintain the opposed members in said second position.

12. The endotracheal tube holder of claim 1 wherein said latch device comprises a plurality of detents associated with one of the opposed members and a detent-engaging structure associated with the other member.

13. An endotracheal tube holder of claim 1 wherein said wings are arranged and dimensioned so that a major portion of each wing is removed from a horizontal plane defined by the longitudinal axis of said lumen and a substantially horizontal line taken radially across said lumen.

14. An endotracheal tube holder comprising:
    a first member that includes a first pair of wing members,
    a first portion disposed between the first pair of wing members,
    a second member, positioned in opposed, spaced relation relative to the first member, that includes a second pair of wing members,
    a second portion disposed between the second pair of wing members,
    the first and second pairs of wing members being dimensioned and arranged so that when the endotracheal tube holder is in a closed position a region of each wing of the first member is adjacent to a region of a corresponding opposed wing of the second member, and the first and second portions being arranged and dimensioned so that when the first and second members are so positioned the first and second portions define a lumen dimensioned to receive the endotracheal tube;
    a hinge constructed to allow the first member to pivot with respect to the second member; and
    a latching device comprising
        a safety clamp disposed in a region of the opposed wings and including a portion which provides interference engagement between the wings to limit the extent to which the first member and second member can pivot about the hinge to a predetermined maximum angle that is sufficiently large to allow the position of the endotracheal tube in the housing to be adjusted axially, and sufficiently small so that the tube cannot be radially displaced from the endotracheal tube holder when the safety clamp is engaged; and
        a securing clamp disposed in a region of the opposed wings and constructed to be movable between a first position, in which the first and second members are allowed to pivot to the extent allowed by the safety clamp, to allow for axial adjustment of the endotracheal tube within the lumen and a second position, in which the first portion and the second portion are sufficiently close to each other to engage the tube and limit axial movement of the tube relative to the endotracheal tube holder.

15. The endotracheal tube holder of claim 14, further comprising a bite block extending axially from the lumen.

16. The endotracheal tube holder of claim 14 wherein the safety and securing clamps comprise a plurality of detents positioned on one of said opposed members and a detent-engaging structure on the opposite opposed member, the detents being positioned for selective engagement of a detent by the detent-engaging structure.

17. The endotracheal tube holder of claim 14 wherein said first portion and said second portion are semi cylindrical, and together define a substantially cylindrical lumen.

18. The endotracheal tube holder of claim 14 wherein said first portion and said second portion are semi-oval in cross-section, and together define a lumen which is substantially oval in cross-section.

19. The endotracheal tube holder of claim 14 wherein said first portion and said second portion are V-shaped in cross-section.

20. The endotracheal tube holder of claim 19 wherein the bite block has a square cross-section.

21. The endotracheal tube holder of claim 19 wherein a soft material, having a durometer rating of 80 or less, covers the bite block.

22. The endotracheal tube holder of claim 14 wherein said first member and said second member are separate, and said hinge comprises a fastener joining said first member and said second member, positioned so that said first and second members can pivot about said hinge.

23. The endotracheal tube holder of claim 14 wherein said first member, second member, and hinge comprise a single unitary part.

24. The endotracheal tube holder of claim 14 wherein said safety clamp comprises a resilient member extending from one of said first and second members towards the opposed member and through an aperture in the opposed member, said resilient member comprising a latch member adapted to engage said upper portion, and a release member which, when deflected, disengages said latch member from said upper portion.

25. The endotracheal tube holder of claim 14 wherein said safety clamp and said securing clamp are on the same side of the lumen defined by the first and second portions.

26. The endotracheal tube holder of claim 25 wherein said safety clamp and said securing clamp are provided by a pair of spaced detents on a single resilient member extending from one of said first and second members, said detents being shaped and positioned to engage a receiving portion of the other of said first and second members.

27. A method of inserting and retaining an endotracheal tube in the tracheal lumen of a patient comprising:

(a) inserting the endotracheal tube through the patient's mouth into the tracheal lumen;

(b) providing an endotracheal tube holder comprising a pair of opposed members constructed to define a lumen when positioned adjacent each other; and a latching device constructed to allow the relative position of the opposed members to be adjusted between a first position in which said lumen is sufficiently small to securely hold the endotracheal tube, and a second position in which the lumen is sufficiently large to allow the endotracheal tube to move axially yet sufficiently small to resist radial displacement of the endotracheal tube;

(c) placing the latching device in its second position;

(d) introducing the endotracheal tube into the lumen defined by the endotracheal tube holder;

(e) adjusting the position of the endotracheal tube holder axially along the length of the endotracheal tube until the endotracheal tube holder is in a desired position; and (f) placing the latching device in its first position, thereby securing the endotracheal tube holder firmly in position on the endotracheal tube.

28. The method of claim 27 further comprising the step of securing the endotracheal tube holder to the patient's head prior to step (e).

* * * * *